United States Patent
Kawase et al.

(10) Patent No.: US 7,291,838 B2
(45) Date of Patent: Nov. 6, 2007

(54) APPARATUS AND METHOD FOR DETECTING SCATTERED MATERIAL BY TERAHERTZ WAVE

(75) Inventors: Kodo Kawase, Wako (JP); Takayuki Shibuya, Wako (JP); Yuichi Ogawa, Wako (JP); Masahiro Yamashita, Matsuyama (JP)

(73) Assignees: Riken, Saitama (JP); S-I Seiko Co., Ltd., Ehime (JP)

( * ) Notice: Subject to any disclaimer, the term of this patent is extended or adjusted under 35 U.S.C. 154(b) by 69 days.

(21) Appl. No.: 11/216,153

(22) Filed: Sep. 1, 2005

(65) Prior Publication Data

US 2006/0043298 A1    Mar. 2, 2006

(30) Foreign Application Priority Data

Sep. 1, 2004    (JP) ............................. 2004-254075

(51) Int. Cl.
*G01J 5/02*    (2006.01)
(52) U.S. Cl. ................. 250/339.06; 250/341.1
(58) Field of Classification Search .......... 250/339.06, 250/338.1, 341.1, 330, 339.09, 208.1; 356/337, 356/336
See application file for complete search history.

(56) References Cited

U.S. PATENT DOCUMENTS

| | | | |
|---|---|---|---|
| 4,121,247 A | 10/1978 | Henry | |
| 6,153,873 A | 11/2000 | Wolf | |
| 6,977,379 B2* | 12/2005 | Zhang et al. | 250/341.1 |
| 7,129,491 B2* | 10/2006 | Ferguson et al. | 250/341.1 |
| 2002/0024718 A1* | 2/2002 | Kawase et al. | 359/330 |
| 2003/0227668 A1* | 12/2003 | Imai et al. | 359/326 |
| 2005/0116170 A1* | 6/2005 | Kawase et al. | 250/341.1 |

FOREIGN PATENT DOCUMENTS

| | | |
|---|---|---|
| EP | 1248092 A2 | 10/2002 |
| JP | 061455/2004 | 2/2004 |
| JP | 108905/2004 | 4/2004 |

OTHER PUBLICATIONS

Yamashita et al., "Non-destructive detection of chemicals by scattering and fingerprinting in the THz band", Joint 29th Int. Conf. on Infrared and Millimeter Waves and 12th Int. Conf. on Terehertz Electronics, 2004, pp. 411-412.

(Continued)

*Primary Examiner*—David Porta
*Assistant Examiner*—Faye Boosalis
(74) *Attorney, Agent, or Firm*—Griffin & Szipl, P.C.

(57) ABSTRACT

There is disclosed an apparatus comprising: a terahertz wave generation device which generates a terahertz wave; a terahertz wave irradiation device which irradiates an object to be inspected with the terahertz wave; and a scattering intensity detection device which cuts a rectilinear wave of the terahertz wave which has passed through the object to be inspected and which detects an intensity of a scattered wave, and a scattered material such as powder or foam contained in an envelope, a capsule, a container or the like is detected in a non-destructive manner without unsealing the envelope or the like.

8 Claims, 5 Drawing Sheets

OTHER PUBLICATIONS

Shibuya et al., "Nondestructive Inspection by Using Scattering and Spectra in Terahertz Waves", IEEJ Trans, EIS, 2005, pp. 545-550, vol. 125, No. 4.

Loeffler et al. "Terahertz dark-field imaging of biomedical tissue", Optics Express, Dec. 3, 2001, pp. 616-621, vol. 9, No. 12.

Jedju et al, "Generation and detection of pulsed T-rays for use in the study of biological and bio-terrorism issues", abstract only.

Jedju et al, "Generation and detection of pulsed T-rays for use in the study of biological and bio-terrorism issues", Terahertz 2004, pp. 92-98, Terahertz for Military and Security Application II, Proceedings of SPIE vol. 5411, Bellingham, WA.

Loeffler et al., "Visualization and classification in biomedical terahertz pulsed imaging", 2002, pp. 3847-3852, Institute of Physics Publishing, Physics in Medicine and Biology, Phys. Med. Biol. 47, IOP Publishing Ltd., UK.

Pearce et al., "Statistics of Multiply Scattered Broadband Terahertz Pulses," week ending Jul. 25, 2003, Physical Review Letters, vol. 91, No. 4, The American Physical Society.

Starrs et al., "Collapse of transient gels in colloid-polymer mixtures", Mar. 18, 2002, pp. 2485-2505, Institute of Physics Publishing, Journal of Physics: Condensed Matter, J. Phys.: Condens. Matter 14, IOP Publishing Ltd., UK.

Choi et al., "Potential for detection of explosive and biological hazards with electronic terahertz systems", Dec. 17, 2003, pp. 337-349, Phil. Trans. R. Soc. Lond. A, The Royal Society.

European Search Report issued in corresponding application No. EP 05 01 8527 completed Nov. 7, 2005 and mailed Dec. 9, 2005.

* cited by examiner

APPARATUS AND METHOD FOR DETECTING SCATTERED MATERIAL BY TERAHERTZ WAVE

This application claims priority from Japanese Patent Application No. 254075/2004, filed Sep. 1, 2004, the entire disclosure of which is incorporated herein by reference.

BACKGROUND OF THE INVENTION

1. Technical Field of the Invention

The present invention relates to an apparatus and method for detecting scattered material such as powder or foam contained in an envelope, a capsule, a container or the like by use of terahertz waves without unsealing the envelope or the like.

2. Description of the Related Art

Hereinafter, electromagnetic waves having frequencies around 1 THz, that is, far-infrared rays and sub-millimeter waves in this frequency region will be called "terahertz waves". The terahertz wave is positioned in a boundary between a light wave and a radio wave, and has characteristics of both of the light and radio waves.

One of the characteristics of the terahertz wave is that it is the shortest wavelength band having material transmitting properties of the radio wave as well as the longest wavelength having straight moving properties of the light wave. More specifically, the terahertz wave is similar to the radio wave in that the wave can pass through various materials. Since the terahertz wave has a short wavelength (around 1 millimeter to 30 micron meters), the wave can obtain the highest spatial resolution in a radio wave band. The terahertz wave is similar to the light wave in that the wave can be treated by lens or mirrors.

Apparatuses utilizing the characteristics of the terahertz waves are described, for example, in Patent Documents 1, 2 and the like.

Figure 1:
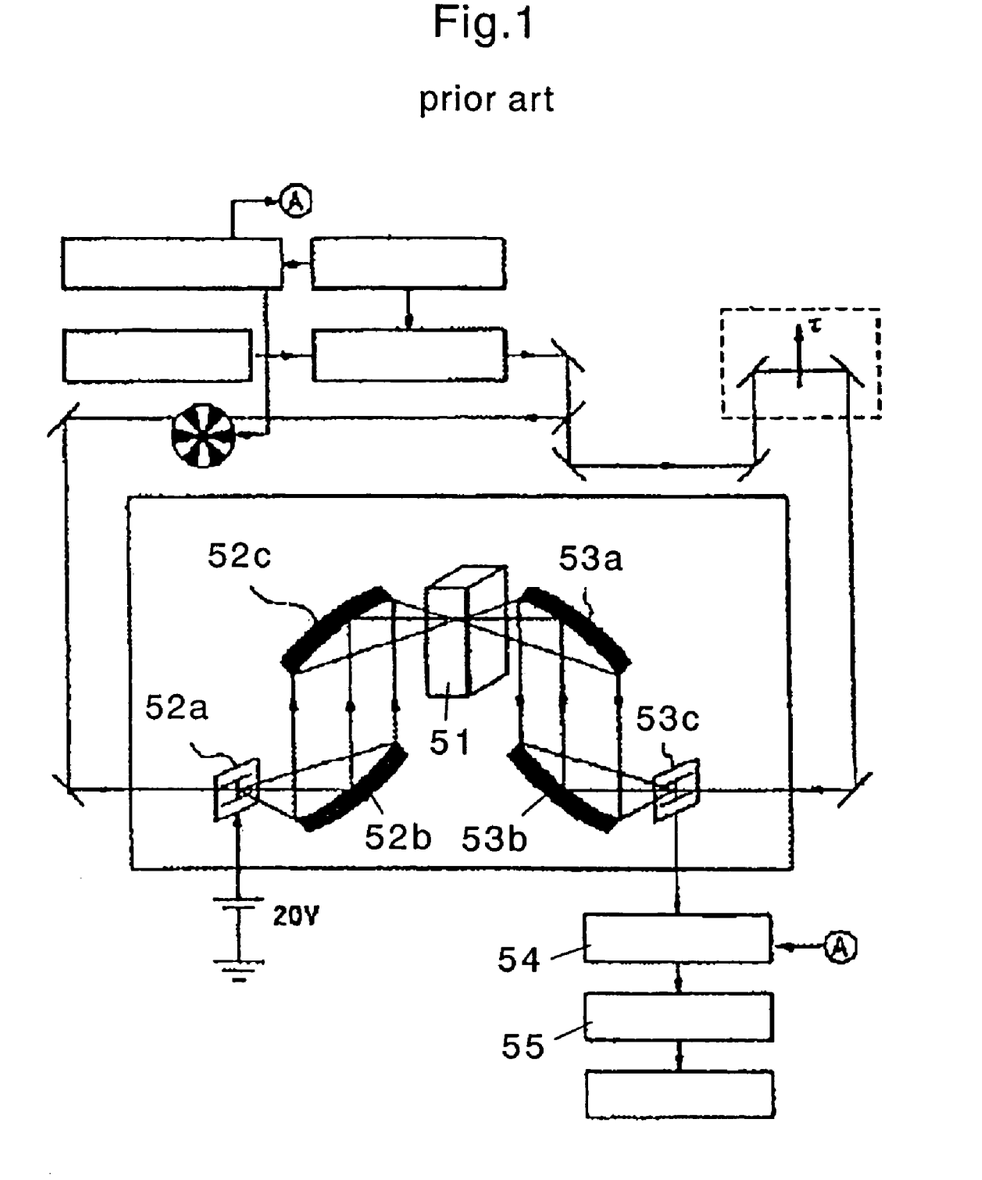
FIG. 1 is a constitution diagram of an apparatus of Patent Document 1.

In "Apparatus and Method for measuring Physical Properties of Powder by means of Terahertz Electromagnetic Wave" of Patent Document 1, as shown in FIG. 1, the apparatus comprises: means 51 for holding powder; irradiation means 52a, 52b, 52c for irradiating the powder with terahertz electromagnetic waves; receiving means 53a, 53b, 53c for receiving the terahertz electromagnetic waves which have passed through the powder to convert the waves into electric signals; means 54 for acquiring from outputs of the receiving means a difference of propagation times or amplitudes between positions of the powder where the terahertz electromagnetic waves pass; and image processing means 55 for processing an image to display the characteristics of the powder in a display based on the difference. The apparatus measures the characteristics of the powder.

In an aspect, a transmittance, a refractive index, a filling ratio and the like of the powder are measured by this means.

Figure 2:
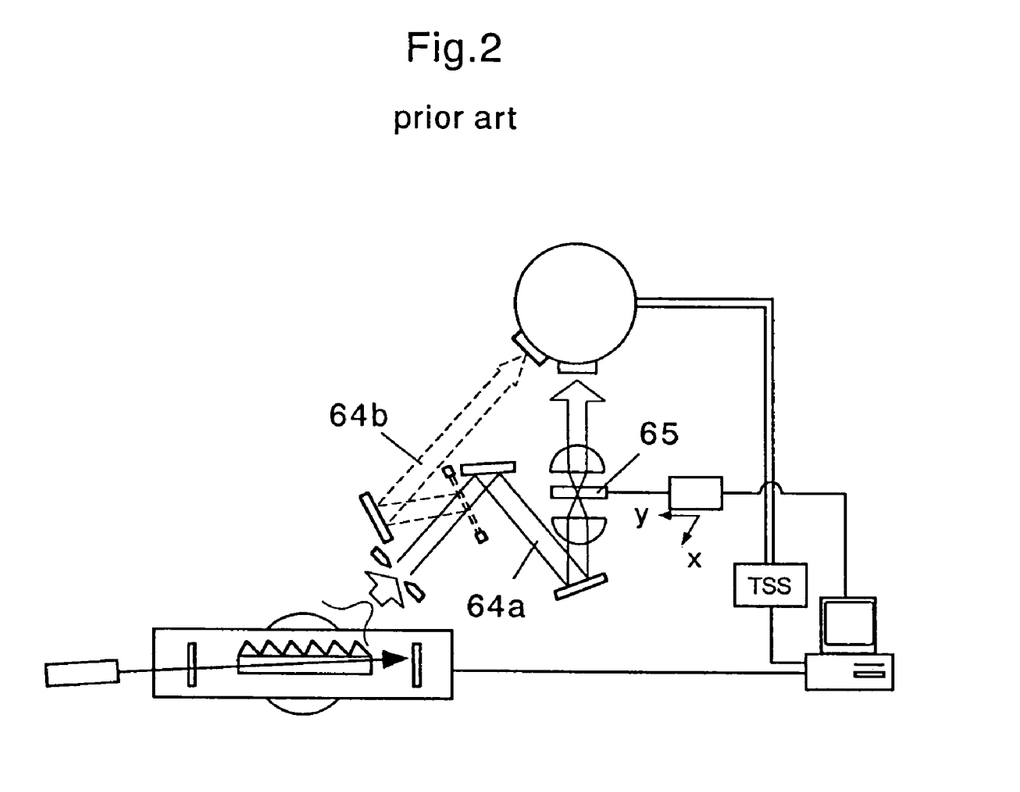
FIG. 2 is a constitution diagram of an apparatus of Patent Document 2.

In "Method and Apparatus for Differential Imaging using Terahertz Wave" of Patent Document 2, as shown in FIG. 2, terahertz waves 64a, 64b on two different wavelengths are generated in a frequency range of about 0.5 to 3 THz, a material 65 to be inspected is irradiated with the terahertz waves on two wavelengths 64a, 64b to measure the transmittances, and presence of a target having dependence of the wavelength on absorption of the terahertz wave is detected from a difference between the transmittances.

In the aspect, the dependence of DNA of salmon or the like on the wavelength is measured by this means.

[Patent Document 1]
Japanese Patent Application Laid-Open No. 2004-61455 titled "Apparatus and Method for measuring Physical Properties of Powder by means of Terahertz Electromagnetic Wave"

[Patent Document 2]
Japanese Patent Application Laid-Open No. 2004-108905 titled "Method and Apparatus for Differential Imaging using Terahertz Wave"

In recent years, one kind of terrorist act has been a social problem in which anthrax bacteria or chemicals are distributed by mail. Conventional X-ray photographs allow shapes of these contents to be determined, but do not allow their properties to be determined unless containers are unsealed. Therefore, for example, when powered chemicals are mailed in an envelope, they cannot be detected unless the envelope is unsealed.

Moreover, even in inspection of products such as medicines, it cannot be detected from the outside whether or not the products are contained in a capsule or a container, unless the capsule or the container is unsealed.

Furthermore, even in a case where foam and the like exist as defects in opaque plastic products, ceramic products, paint, petroleum, glaze, magnetic paint and the like, the defects cannot be heretofore detected from the outside in a non-destructive manner.

SUMMARY OF THE INVENTION

The present invention has been developed to solve the problems. That is, an object of the present invention is to provide a scattered material detection apparatus and method capable of detecting a scattered material such as powder or foam contained in an envelope, a capsule, a container or the like in a non-destructive manner without unsealing the envelope or the like by use of a terahertz wave.

The terahertz wave has a high transmitting property through the envelope, a plastic container or the like, and usually rectilinearly passes therethrough as such. On the other hand, in the presence of the powder or the foam in the container, the terahertz wave is usually intensely scattered because of its short wavelength. Therefore, when a rectilinear wave and a scattered wave of terahertz light are measured separately from each other, it is possible to detect the presence of the scattered material such as the powder or the foam in the envelope or the plastic container. The present invention is based on such inventive finding.

That is, according to the present invention, there is provided a scattered material detection apparatus using a terahertz wave, comprising: a terahertz wave generation device which generates the terahertz wave; a terahertz wave irradiation device which irradiates an object to be inspected with the terahertz wave; and a scattering intensity detection device for cutting a rectilinear wave of the terahertz wave which has passed through the object to be inspected and for detecting an intensity of a scattered wave.

According to a preferable aspect of the present invention, the terahertz wave irradiation device comprises: a lens which converts the generated terahertz wave into parallel light; and an iris diaphragm which limits a sectional shape of the parallel light, to be smaller than that of the object to be inspected to irradiate the object with the light.

The scattering intensity detection device comprises: a confocal optical system for interrupting the terahertz wave which has rectilinearly passed through the object to be inspected midway and for focusing the terahertz wave scattered by the object to be inspected in a predetermined position; and a scattering intensity detection unit which detects the intensity of the terahertz wave in the focal position.

The confocal optical system comprises: first and second off-axis parabolic mirrors which face each other; and a shielding member which is positioned between the two off-axis parabolic mirrors and which cuts the rectilinear wave of the terahertz wave and which transmits the scattered wave. The first off-axis parabolic mirror has an incidence-side focus and a reflection-side focus along an axial line of the terahertz wave, the object to be inspected is positioned in the incidence-side focus of the first off-axis parabolic mirror or its vicinity, and the shielding member is positioned in the reflection-side focus of the first off-axis parabolic mirror or its vicinity.

According to another preferable aspect of the present invention, the confocal optical system comprises: first and second convex lenses which face each other; and a shielding member which is positioned between two convex lenses and which cuts the rectilinear wave of the terahertz wave and which transmits the scattered wave. The first convex lens has an incidence-side focus and an outlet-side focus along an axial line of the terahertz wave, the object to be inspected is positioned in the incidence-side focus of the first convex lens or its vicinity, and the shielding member is positioned in the outlet-side focus of the first convex lens or its vicinity.

Moreover, according to the present invention, there is provided a scattered material detection method using a terahertz wave, comprising: a terahertz wave generating step of generating the terahertz wave; a terahertz wave irradiating step of irradiating an object to be inspected with the terahertz wave; and a scattering intensity detecting step of cutting a rectilinear wave of the terahertz wave which has passed through the object to be inspected and detecting an intensity of a scattered wave.

According to a preferable aspect of the present invention, in the terahertz wave irradiating step, the terahertz wave generated in the terahertz wave generating step is converted into parallel light, and a sectional shape of the parallel light is limited to be smaller than that of the object to be inspected to irradiate the object with the light.

In the scattering intensity detecting step, the terahertz wave which has rectilinearly passed through the object to be inspected is interrupted midway, the terahertz wave scattered by the object to be inspected is focused in a predetermined position, and the intensity of the terahertz wave in the focal position is detected.

According to the apparatus and the method of the present invention, superior effects are produced. For example, the rectilinear wave of the terahertz wave which has passed through the object to be inspected can be cut, and the intensity of the scattered wave can be detected. Therefore, a scattered material such as powder or foam contained in an envelope, a capsule, a container or the like can be detected in a non-destructive manner without unsealing the envelope or the like.

Other objects and advantageous characteristics of the present invention will be apparent from the following description with reference to the accompanying drawings.

DESCRIPTION OF THE PREFERABLE EMBODIMENTS

Preferable embodiments of the present invention will be described hereinafter with reference to the drawings. It is to be noted that in the drawings, common parts are denoted with the same reference numerals to avoid redundant description.

Figure 3:
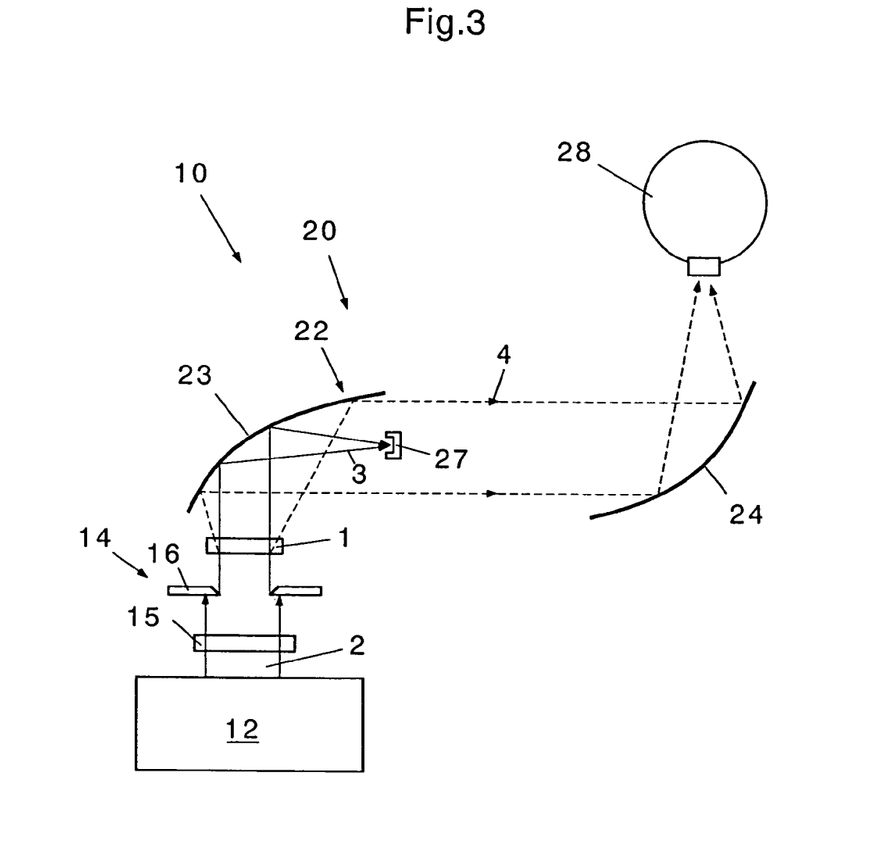
FIG. 3 is a configuration diagram of a first embodiment of a scattered material detection apparatus of the present invention.

FIG. 3 is a configuration diagram of a first embodiment of a scattered material detection apparatus of the present invention. As shown in the figure, a scattered material detection apparatus 10 of the present invention is provided with a terahertz wave generation device 12, a terahertz wave irradiation device 14, and a scattering intensity detection device 20.

The terahertz wave generation device 12 generates a terahertz wave 2. The terahertz wave 2 has a constant wavelength in a range of around 1 millimeter to 30 micron meter, and is preferably a continuous or pulse wave having a certain output. A generation source of the generated terahertz wave may be a spot light source, a linear light source, or a parallel light source.

The terahertz wave irradiation device 14 irradiates an object 1 to be inspected with the terahertz wave 2. The terahertz wave irradiation device 14 comprises: a lens 15 which converts the generated terahertz wave 2 into parallel light; and an iris diaphragm 16 which limits a sectional shape of the parallel light to be smaller than that of the object 1 to be inspected to irradiate the object with the light.

In this embodiment, the generation source of the terahertz wave 2 is the linear light source which is parallel to a drawing sheet surface, and the lens 15 is a cylindrical lens which extends in parallel with the sheet surface. The generation source of the terahertz wave 2 is positioned in a linear focal position of the cylindrical lens 15, and the wave is converted into the parallel light whose sectional shape is rectangular by means of the cylindrical lens 15.

The iris diaphragm 16 has a rectangular aperture which is smaller than the object 1 to be inspected, the output of the terahertz wave 2 with which the object 1 to be inspected is irradiated is kept to be constant, and the object 1 to be inspected is irradiated with a total quantity of output.

It is to be noted that the lens 15 is not limited to this constitution, and a usual convex lens system may be used with respect to the spot light source. The iris diaphragm 16 is not limited to this constitution, and may be a circular or rectangular variable diaphragm.

The scattering intensity detection device 20 cuts a rectilinear wave 3 of the terahertz wave 2 which has passed through the object 1 to be inspected to detect an intensity of a scattered wave 4. The scattering intensity detection device 20 comprises: a confocal optical system 22 for interrupting the terahertz wave 2 which has rectilinearly passed through the object 1 to be inspected midway and for condensing the terahertz wave 2 scattered by the object 1 to be inspected in a predetermined position; and a scattering intensity detection unit 28 which detects the intensity of the terahertz wave in the focal position.

Figure 4:
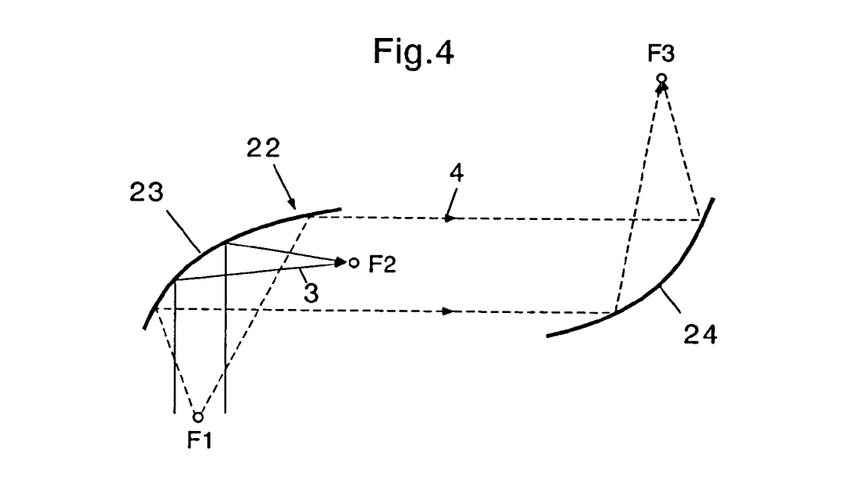
FIG. 4 is an explanatory view of a confocal optical system of FIG. 3.

FIG. 4 is an explanatory view of the confocal optical system of FIG. 3. In this figure, the confocal optical system 22 comprises: first and second off-axis parabolic mirrors 23, 24 which face each other; and a shielding member 27 which is positioned between the two off-axis parabolic mirrors and which cuts the rectilinear wave 3 of the terahertz wave and which transmits the scattered wave 4.

Each of the first and second off-axis parabolic mirrors 23, 24 is a concave reflective mirror having a parabolic reflective surface as viewed on the drawing sheet. The focal positions may be the same or different.

The first off-axis parabolic mirror 23 has an incidence-side focus F1 and a reflection-side focus F2 along an axial line of the terahertz wave 2. The object 1 to be inspected is positioned in the incidence-side focus F1 of the first off-axis parabolic mirror 23 or its vicinity. The shielding member 27 is positioned in the reflection-side focus F2 of the first off-axis parabolic mirror 23 or its vicinity.

According to this constitution, in the rectangular parallel light 2 with which the object 1 to be inspected has been irradiated, the rectilinear wave 3 which has passed through the object 1 to be inspected as such is reflected by the first off-axis parabolic mirror 23, concentrated on the reflection-side focus F2, and cut by the shielding member 27. The shielding member 27 is preferably sufficiently small, and has a small reflectance of the terahertz wave 2 as long as this function is satisfied.

Moreover, in the rectangular parallel light 2 with which the object has been irradiated, the scattered wave 4 scattered by the object 1 to be inspected is reflected by the first and second off-axis parabolic mirrors 23, 24, and concentrated on the reflection-side focus F3 of the second off-axis parabolic mirror 24.

The scattering intensity detection unit 28 is, for example, a silicon bolometer, and detects the intensity of the terahertz wave 2 concentrated on the reflection-side focus F3 of the second off-axis parabolic mirror 24.

Therefore, according to this constitution, the rectilinear wave 3 can be cut, and the intensity of the scattered wave 4 can be detected.

Figure 5:
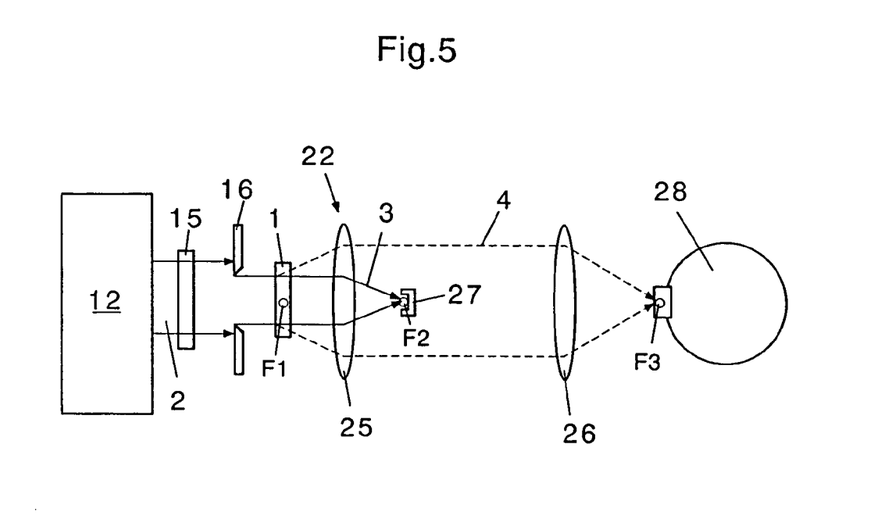
FIG. 5 is a configuration diagram of a second embodiment of the scattered material detection apparatus of the present invention.

FIG. 5 is a configuration diagram of a second embodiment of the scattered material detection apparatus of the present invention. In this embodiment, a confocal optical system 22 comprises: first and second convex lenses 25, 26 which face each other; and a shielding member 27 which is positioned between two convex lenses and which cuts a rectilinear wave 3 of a terahertz wave 2 and which transmits a scattered wave 4.

Each of the first and second convex lenses 25, 26 may be a single or composite lens. The lens may be a circular lens focusing on one point or a linearly focusing cylindrical lens. Focal distances of the lenses may be equal or different.

The first convex lens 25 has an incidence-side focus F1 and an outlet-side focus F2 along an axial line of the terahertz wave 2. The object 1 to be inspected is positioned in the incidence-side focus F1 of the first convex lens 25 or its vicinity, and the shielding member 27 is positioned in the outlet-side focus F2 of the first convex lens 25 or its vicinity.

The parallel light 2 with which an object 1 to be inspected is irradiated may be rectangular or circular. Another constitution is similar to that of FIG. 4.

According to this constitution, in the parallel light 2 with which the object 1 to be inspected has been irradiated, the rectilinear wave 3 which has passed through the object 1 to be inspected as such is concentrated on the outlet-side focus F2 of the first convex lens 25, and cut by the shielding member 27. In the parallel light 2 with which the object has been irradiated, the scattered wave 4 scattered by the object 1 to be inspected is concentrated on the outlet-side focus F3 of the second convex lens 26. Therefore, according to this constitution, the rectilinear wave 3 can be cut, and the intensity of the scattered wave 4 can be detected.

Figure 6:
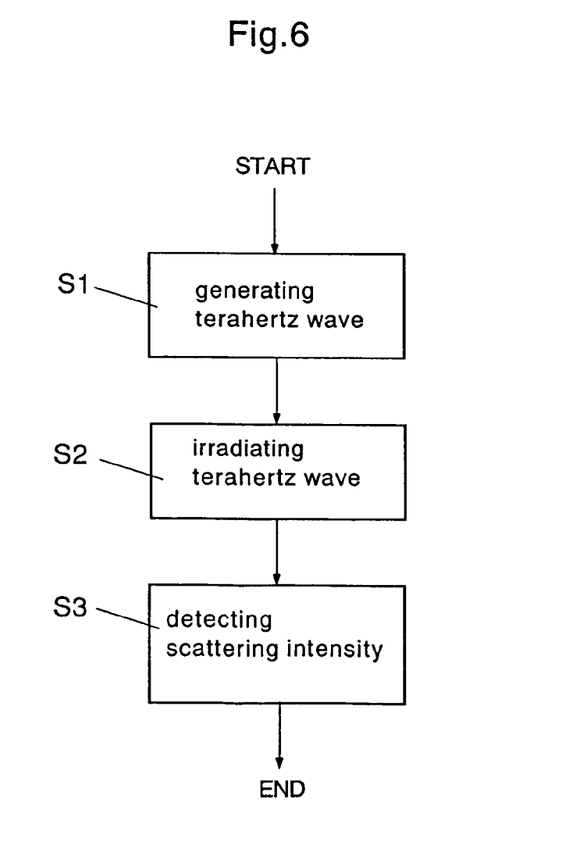
FIG. 6 is a flowchart of a scattered material detection method of the present invention.

FIG. 6 is a flowchart of a scattered material detection method of the present invention. The method of the present invention is performed in the following steps by use of the apparatus described above with reference to FIGS. 3 to 5.

In a terahertz wave generating step S1, a terahertz wave 2 is generated.

In a terahertz wave irradiating step S2, an object 1 to be inspected is irradiated with the generated terahertz wave 2.

In a scattering intensity detecting step S3, a rectilinear wave 3 of the terahertz wave 2 which has passed through the object 1 to be inspected is cut, and an intensity of a scattered wave 4 is detected.

It is to be noted that in the terahertz wave irradiating step S2, the terahertz wave 2 generated in the terahertz wave generating step S1 is converted into parallel light, next a sectional shape of the parallel light is limited to be smaller than that of the object 1 to be inspected, and the object may be irradiated with the light.

Moreover, in the scattering intensity detecting step S3, the terahertz wave 2 which has rectilinearly passed through the object 1 to be inspected is interrupted midway, the terahertz wave 2 scattered by the object 1 to be inspected is concentrated in a predetermined position, and the intensity of the terahertz wave in the focal position may be detected.

Examples of the present invention will be described hereinafter.

EXAMPLE 1

Figure 7:
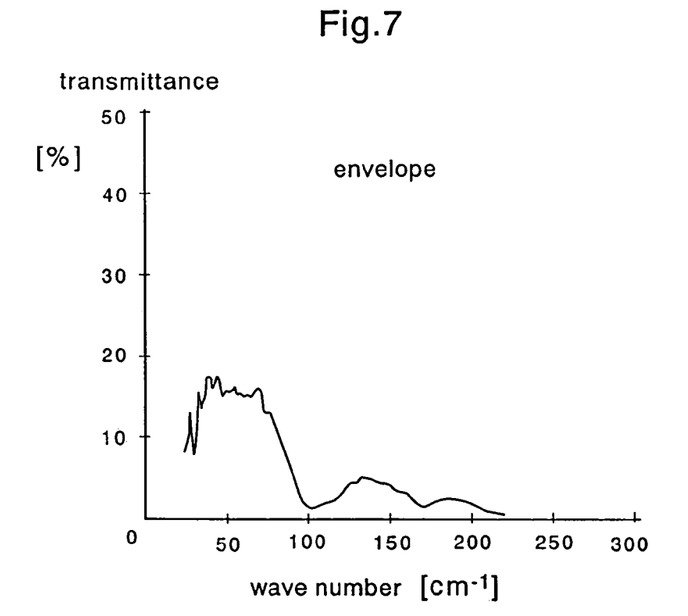
FIG. 7 shows measurement results of transmittances according to the first embodiment of the present invention.

FIG. 7 shows an example in which a transmittance of an electromagnetic wave with respect to an empty envelope is measured. In this figure, the abscissa indicates the wave number, and the ordinate indicates the transmittance. The used envelope is commercially available for airmailing. It is to be noted that the wave number [$cm^{-1}$] is an inverse number of a wavelength.

It is seen from this figure that when the wave number exceeds 70 $cm^{-1}$, the transmittance drops. It is to be noted that this result is not limited to that of paper, and a similar result is obtained even from a capsule, a plastic container or the like.

On the other hand, in general, the shorter the wavelength is and the larger the wave number is, the higher a resolution with respect to the object becomes. Therefore, as an electromagnetic wave for use in irradiating the object to be inspected, a terahertz wave is preferably used whose wave number is preferably in a range of 30 to 70, that is, the wavelength is in a range of 0.1 to 0.3 mm.

EXAMPLE 2

Intensities of scattered light were measured using an apparatus shown in FIG. 3 only with an envelope and in a case where powder was introduced in the envelope.

In this test, a terahertz wave generation device 12 for generating a terahertz wave 2 of 1.5 THz was used. A wavelength was about 0.2 mm. As first and second off-axis parabolic mirrors 23, 24, concave reflective mirrors were used whose focal distances were 50.8 mm and 76.4 mm, respectively.

As the powder, powder of sugar (fructose) was used in consideration of a pre-stage inspection of an inspection of presence of prohibited chemicals in the envelope. The powder having particle diameters of 1 mm to 30 micron meter was prepared, divided into four types of particle diameter ranges, and tested.

Figure 8:
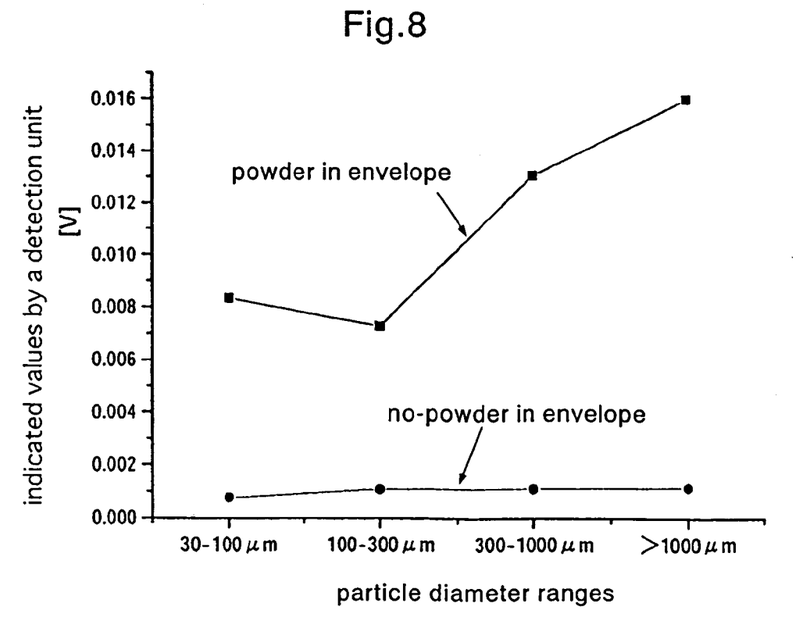
FIG. 8 shows measurement results of scattering intensities according to the second embodiment of the present invention.

FIG. 8 shows obtained measurement results of scattering intensities. In this figure, the abscissa indicates four types of particle diameter ranges in order from the largest particle, and the ordinate indicates values indicated by a detection unit (scattering intensity detection unit 28).

It has been confirmed from this result that the powder in the envelope can be identified using this apparatus. It is to be noted that the present invention is not limited to the powder, and is applicable to judgment of presence of such non-uniform materials as to cause scattering, such as medical chemical products contained in capsules or containers, and foam inside opaque plastic products, ceramic products, paint, petroleum, glaze, and magnetic paint.

It is to be noted that the present invention is not limited to the above-described examples and embodiments, and can be, needless to say, variously changed within a range that does not depart from the scope of the present invention.

What is claimed is:

1. A scattered material detection apparatus using a terahertz wave, comprising:
    (a) terahertz wave generation device which generates the terahertz wave;
    (b) a terahertz wave irradiation device which irradiates an object to be inspected with the terahertz wave, wherein the terahertz wave irradiation device comprises
        i. a lens that converts the generated terahertz wave into parallel light; and
        ii. an iris diaphragm that limits a sectional shape of the parallel light to be smaller than that of the object to be inspected to irradiate the object with light; and
    (c) a scattering intensity detection device for cutting a rectilinear wave of the terahertz wave which has passed through the object to be inspected and for detecting an intensity of a scattered wave, wherein the scattering intensity detection device comprises
        i. a confocal optical system for interrupting the terahertz wave that has rectilinearly passed through the object to be inspected midway and for focusing the terahertz wave scattered by the object to be inspected in a predetermined position; and
        ii. a scattering intensity detection unit that detects the intensity of the terahertz wave in the focal position.

2. The scattered material detection apparatus according to claim 1, wherein the confocal optical system comprises: first and second off-axis parabolic mirrors which face each other; and a shielding member which is positioned between the two off-axis parabolic mirrors and which cuts the rectilinear wave of the terahertz wave and which transmits the scattered wave, the first off-axis parabolic mirror has an incidence-side focus and a reflection-side focus along an axial line of the terahertz wave, the object to be inspected is positioned in the incidence-side focus of the first off-axis parabolic mirror or in the vicinity of the incidence-side focus, and the shielding member is positioned in the reflection-side focus of the first off-axis parabolic mirror or in the vicinity of the reflection-side focus.

3. The scattered material detection apparatus according to claim 2, wherein the terahertz wave generation device comprises a linear light source and the lens is a cylindrical lens that extends in parallel with the object.

4. The scattered material detection apparatus according to claim 1, wherein the confocal optical system comprises: first and second convex lenses which face each other; and a shielding member which is positioned between two convex lenses and which cuts the rectilinear wave of the terahertz wave and which transmits the scattered wave, the first convex lens has an incidence-side focus and an outlet-side focus along an axial line of the terahertz wave, the object to be inspected is positioned in the incidence-side focus of the first convex lens or in the vicinity of the incidence-side focus, and the shielding member is positioned in the outlet-side focus of the first convex lens or in the vicinity of the outlet-side focus.

5. The scattered material detection apparatus according to claim 4, wherein the terahertz wave generation device comprises a linear light source and the lens is a cylindrical lens that extends in parallel with the object.

6. The scattered material detection apparatus according to claim 1, wherein the terahertz wave generation device comprises a linear light source and the lens is a cylindrical lens that extends in parallel with the object.

7. A scattered material detection method using a terahertz wave, comprising:

a terahertz wave generating step of generating the terahertz wave;

a terahertz wave irradiating step of irradiating an object to be inspected with the terahertz wave; and a scattering intensity detecting step of cutting a rectilinear wave of the terahertz wave which has passed through the object to be inspected and detecting an intensity of a scattered wave, wherein in the terahertz wave irradiating step, the terahertz wave generated in the terahertz wave generating step is converted into parallel light, and a sectional shape of the parallel light is limited by an iris diaphragm to be smaller than that of the object to be inspected to irradiate the object with the light, and in the scattering intensity detecting step, the terahertz wave which has rectilinearly passed through the object to be inspected is interrupted midway, the terahertz wave scattered by the object to be inspected is focused in a predetermined position, and the intensity of the terahertz wave in the focal position is detected.

8. A scattered material detection method using a terahertz wave, comprising the steps of:
    (a) generating a terahertz wave;
    (b) irradiating an object to be inspected with the terahertz wave; and
    (c) cutting a rectilinear wave of the terahertz wave that has passed through the object to be inspected and detecting an intensity of a scattered wave, wherein when irradiating the object to be inspected the terahertz wave is converted into parallel light, and a sectional shape of the parallel light is limited by an iris diaphragm to be smaller than that of the object to be inspected to irradiate the object with the light, and the terahertz wave that has rectilinearly passed through the object to be inspected is interrupted midway, and the terahertz wave scattered by the object to be inspected is focused in a predetermined position so that intensity of the terahertz wave in the focal position is detected.

* * * * *